Figure 1:
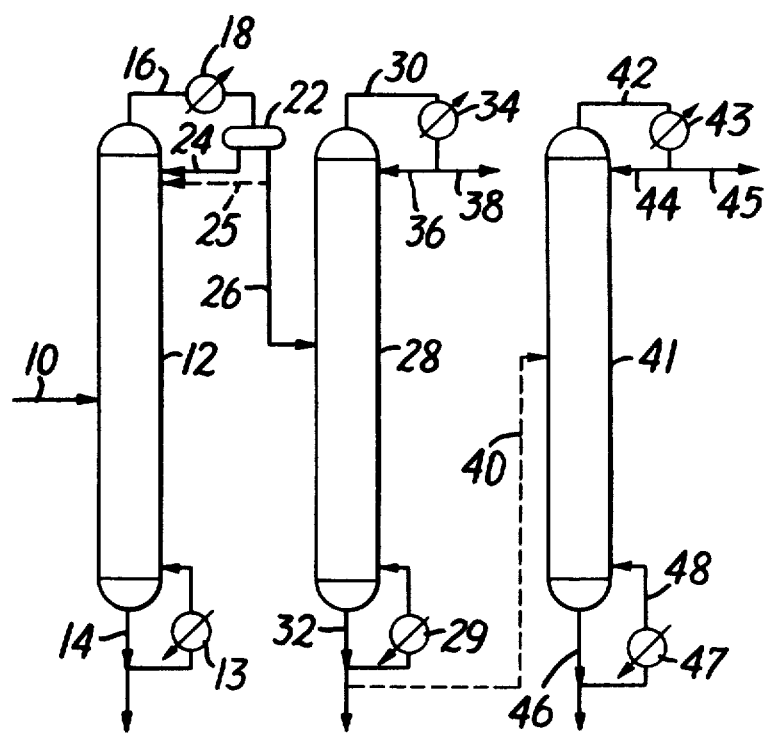

United States Patent [19]

Becker et al.

[11] 4,045,294
[45] Aug. 30, 1977

[54] PROCESS FOR THE RECOVERY OF ALKYLENE GLYCOLS

[75] Inventors: Mitchell Becker, Teaneck; Jon R. Valbert, Ridgewood, both of N.J.

[73] Assignee: Halcon International, Inc., New York, N.Y.

[21] Appl. No.: 612,824

[22] Filed: Sept. 12, 1975

[51] Int. Cl.² .................. B01D 3/36; C07C 29/28
[52] U.S. Cl. .................. 203/69; 203/81; 260/637 R
[58] Field of Search ........... 203/69, 52, 68, 81, 203/70; 260/637 R

[56] References Cited

U.S. PATENT DOCUMENTS

| | | | |
|---|---|---|---|
| 3,066,116 | 11/1962 | Schiller et al. | 203/69 |
| 3,074,962 | 1/1963 | Anderson | 203/69 |
| 3,437,566 | 4/1969 | Gasser et al. | 203/69 |
| 3,809,724 | 5/1974 | Golden | 260/637 R |

OTHER PUBLICATIONS

Horsley: Azeotropic Data III (1973), pp. 147; 207–208.
Weissberger: Technique of Organic Chemistry, vol. IV – Distillation pp. 359–372.

Primary Examiner—Wilbur L. Bascomb, Jr.
Attorney, Agent, or Firm—William C. Long; David Dick; Riggs T. Stewart

[57] ABSTRACT

Ethylene glycol or 1,2-propylene glycol contained in mixtures with lower carboxylate esters of the glycol is recovered by azeotropic distillation of the mixtures with an azeotroping agent which is a hydrocarbon which has a boiling point at atmospheric pressure above 190° C but at most about 220° C and is free from linear secondary and tertiary hydrogen atoms.

4 Claims, 2 Drawing Figures

PROCESS FOR THE RECOVERY OF ALKYLENE GLYCOLS

This invention relates to the recovery of ethylene glycol or 1,2-propylene glycol from mixtures containing the glycol in admixture with lower carboxylate esters of the glycol, i.e., the ethylene or propylene glycol monocarboxylate and/or the ethylene or propylene glycol dicarboxylate. The invention is more particularly concerned with the recovery of the glycol from mixtures produced by the hydrolysis of lower carboxylate esters of the glycol.

Ethylene glycol and 1,2-propylene glycol (hereafter referred to as propylene glycol) are chemicals of acknowledged commercial importance. Ethylene glycol is used, for example, in the preparation of anti-freeze compositions and in the manufacture of polyester fibers. Ethylene glycol manufacturing processes of commercial interest have generally been based upon ethylene oxide as a raw material. Recently, however, processes have been developed which make it possible to produce ethylene glycol and propylene glycol without the necessity for the intermediate manufacture of the oxide. These processes employ the liquid phase reaction of the olefin, a carboxylic acid and molecular oxygen in the presence of a catalyst to produce carboxylic acid esters of ethylene or propylene glycol. A process of this type is disclosed in Belgian Pat. No. 738,104. The glycol can be liberated by hydrolysis of the carboxylate esters produced in these processes. However, the conversion of the esters to the glycol is limited by equilibria and the recovery and separation of the glycol produced in the hydrolysis reaction from the unconverted carboxylate esters involves many difficulties because of the formation of glycol-carboxylate ester azeotropes.

It is an object of this invention to provide a process for the effective recovery of ethylene glycol or propylene glycol from mixtures of the glycol with lower carboxylate esters of the glycol.

It is an additional object of this invention to provide a process for the effective recovery of ethylene or propylene glycol produced by the hydrolysis of lower carboxylate esters of the glycol.

It is a further object of the invention to provide a process for the separation of ethylene or propylene glycol from reaction mixtures produced by the hydrolysis of lower carboxylate esters of the glycol which can be integrated with the hydrolysis step itself.

Other objects of the invention will be apparent from the following description of the invention and of illustrative embodiments thereof.

The following description is presented with reference to ethylene glycol, it being understood that the description is equally and fully applicable to propylene glycol.

In accordance with the invention, ethylene glycol is separated from mixtures thereof with lower carboxylate esters of ethylene glycol, such as those produced by the hydrolysis of lower carboxylate esters of ethylene glycol, by distilling such mixtures in the presence of a hydrocarbon azeotroping agent which is essentially water-immiscible and forms a minimum-boiling azeotrope with ethylene glycol, and which has a boiling point at atmospheric pressure of more than 190° and at most about 220° C, most preferably about 190° to about 215° C, and which is free from linear secondary or tertiary carbon atoms contained in an open chain. It has been discovered that when the ethylene glycol-containing mixture is distilled in the presence of such azeotroping agents, the tendence of ethylene glycol to form azeotropes with the mono-and di-ethylene glycol carboxylates is no longer a hindrance to the separation of ethylene glycol from the mixture and the azeotrope with the added azeotroping agent thus can be readily removed by distillation from the mixture, and the ethylene glycol can be easily recovered from it in a pure form. The distillate, when condensed, separates into phases, viz., a phase composed essentially of the azeotroping agent and a phase containing the ethylene glycol. The phase containing the azeotroping agent is readily separated, as by decantation, from the ethylene-glycol-containing phase and is returned to the distillation column as reflux. Consequently, the azeotroping agent is merely recirculated in the distillation system and the originally-supplied quantity of azeotroping agent is continually available for reuse except for the very small normally-encountered handling losses which are compensated for by the addition of make-up azeotroping agent to the system.

The azeotropic distillation of mixtures of ethylene glycol or propylene glycol with lower carboxylate esters of the glycol to separate the glycol from such esters has been proposed in Golden U.S. Pat. No. 3,809,924, the disclosure of which is incorporated herein by reference. That patent refers to the use of azeotropic agents having atmospheric boiling points in the range of 135° to 190° C and names a number of agents suitable for the azeotropic distillation. While effective separation of the glycol is obtained by the azeotroping agents disclosed in that patent, the agents vary from one another in the extent of separation which they effect, particularly the separation of the glycol from the glycol monoester and they vary among one another in the percentage of glycol in the azeotrope removed as distillate. It has now been discovered that azeotroping agents of the character described above which have atmospheric boiling points above 190° C and at most about 220° C form azeotropes with these glycols having a relatively high content of the respective glycols, and are particularly effective in separating the glycol from the contaminating glycol esters, particularly the problem monoester, and the use of these azeotroping agents makes possible the recovery of a glycol of high purity, as evidenced by favorable ultra violet characteristics. In other words, the surprising discovery has been made that these agents have an unexpected activity when used to separate ethylene glycol or propylene glycol from associated glycol esters.

Most advantageously, the azeotroping agents of this invention are alkylated benzenes. An especially preferred azeotroping agent is p-tert-butyl toluene. Table A below identifies examples of azeotroping agents of this invention and indicates the boiling point of the azeotrope with ethylene glycol.

TABLE A

| Azeotroping Agent | Azeotrope b.p., ° C 760 mm. Hg | Agent b.p., ° C 760 mm. Hg |
|---|---|---|
| p-tert.-butyl toluene | 173 | 193 |
| Durene | 174 | 194 |
| Isodurene | 175 | 197 |
| Prehnitene | 176 | 204 |
| Tetralin | 178 | 207.2 |

The separation process of the invention is applicable to the recovery of ethylene glycol from mixtures of this compound with ethylene glycol lower carboxylate esters produced in any manner, but it is of particular utility in the separation of ethylene glycol from such mixtures produced by the hydrolysis of mono- and or dicarboxylate esters of ethylene glycol and the separation process can be readily integrated with the hydrolysis operation. The ethylene glycol-ester feed which is fed to the azeotropic distillation operation of this invention is a mixture of ethylene glycol with lower carboxylate monoesters or diesters of ethylene glycol, i.e., esters of ethylene glycol and an alkanoic acid having from 1 to 6 carbon atoms per molecule, such as formic acid, acetic acid, propionic acid, butyric acid, isobutyric acid, and the valeric and caproic acids. Accordingly, the lower carboxylate monoesters of ethylene glycol include ethylene glycol monoformate, ethylene glycol monoacetate, ethylene glycol monopropionate, ethylene glycol monobutyrate, ethylene glycol monoisobutyrate, the ethylene glycol monovalerates and the ethylene glycol monocaproates, and the diesters include the corresponding diesters of the same alkanoic acids. Ethylene glycol admixed with the ethylene glycol monoformate, ethylene glycol monoacetate, monopropionate, monobutyrate and monoisobutyrate, the corresponding diesters, mixtures of such monoesters and such diesters, are typical feedstocks and the diacetate-monoacetate mixtures are particularly typical feedstocks. Of course, the ethylene glycol to be separated can also be present in mixtures of esters such as mixtures of ethylene glycol monoacetate and ethylene glycol monoformate, as well as mixtures with one or more diesters, including mixed diesters such as ethylene glycol acetate formate. As used herein, therefore, the term "ethylene glycol-ester feed" is intended to include not only mixtures of ethylene glycol with the lower carboxylate ethylene glycol monoester alone or the ethylene glycol diester alone but also mixtures of different ethylene glycol carboxylate esters. In general, mixtures containing the ethylene glycol may contain small amounts of by-products associated with the preparation of the glycol ester. Such by-products would normally include small quantities of water and acids and may also include catalyst residues and aldehydic by-products, such as, for example, acetaldehyde and formaldehyde.

The azeotropic distillation process of this invention is particularly applicable to ethylene glycol-ester mixtures containing 5 to 95 mol percent of ethylene glycol.

The distillation unit in which the azeotropic distillation of the invention is carried out can be any convenient fractional distillation unit, e.g., a plate column or a packed column, having a sufficient number of theoretical plates for the desired separation, generally from 15 to 50 theoretical plates. The temperature will, of course, vary with the particular azeotroping agent, since each agent forms a minimum-boiling binary azeotrope with ethylene glycol having a different boiling point but, in general, pot temperatures of 190° to 210° C at 760 mm.Hg are employed in the distillation. Similarly, pressures of from 400 mm.Hg to 50 psig are suitably employed. The distillate, when condensed, separates into a first phase, which is the upper phase, composed primarily of the azeotroping agent, and into a second phase, i.e., a lower phase composed primarily of ethylene glycol. This ethylene glycol phase may contain small amounts of ethylene glycol monocarboxylate esters which, when present in the system, will tend to distill with the azeotropic mixture. The vapor condensate from the azeotropic distillation operation is suitably passed to a separator or decanter and the azeotroping agent-containing phase is returned as reflux to the distillation column. It will be understood, however, that operation outside the above-mentioned temperature and pressure ranges is possible and the specific choice of specific combinations of conditions is entirely within the scope of persons skilled in the art. Preferably, as disclosed in the application of Chun Fei Chueh, being filed on even date herewith, and identified as Case 1088, the disclosure of which application is incorporated herein by reference, a controlled quantity of the glycol-containing phase is also returned to the distillation column as reflux. The minimum reflux ratio of the glycol-containing phase is typically 0.3:1, preferably 0.5:1, and most preferably 1:1. From a practical standpoint the reflux ratio of the glycol-containing phase is generally not above 8:1 although it can be higher if desired. Preferably, all of the phase containing the azeotroping agent is returned to the distillation column as reflux. When both the azeotroping agent and the product glycol are refluxed to the distillation zone in this manner there is a significant improvement in the purity of the glycol removed as distillate.

Ethylene glycol is recovered from the ethylene glycol phase by distillation, extraction, or other appropriate means, although fractional distillation is preferred. Suitably, the ethylene glycol-containing phase from the azeotropic condensate is subjected to further fractional distillation to remove an overhead comprising any ethylene glycol monocarboxylate ester which may be present along with a relatively small amount of ethylene glycol, together with any azeotroping agent which may be present, and substantially pure ethylene glycol is withdrawn as bottoms product. Typically, the glycol-containing phase from the azeotropic distillation will be substantially free from that glycol diesters contained in the feed to the azeotropic distillation but glycol monoesters will be present since, although undergoing substantial separation in the azeotropic distillation, they tend to pass in part into the overhead and this is particularly true of acetates and formates, especially formates. The further fractional distillation, however, effectively removes these monoesters and makes possible the ready recovery as bottoms product of substantially pure ethylene glycol. This distillation is carried out under appropriate distillation conditions, most suitably at pot or reboiler temperatures of 120° to 210° C and pressures of 50 mm.Hg to 7 psig. Any azeotropic agent present in the overhead from this last-mentioned distillation step will generally phase separate and is advantageously recycled by combining it with the feed to the azeotropic distillation column. The glycol-ester phase can be recycled to the hydrolysis step when the azeotropic distillation of the invention is integrated with the hydrolysis of glycol esters.

As previously mentioned, the ethylene glycol recovery process of this invention is particularly adapted to be integrated with the hydrolysis of ethylene glycol lower carboxylate esters, i.e., ethylene glycol lower carboxylate monoesters, diesters and mixtures of monoesters and diesters, i.e., it can follow the hydrolysis operation in order to recover the ethylene glycol which is produced. Thus, the ethylene glycol-ester feed to the azeotropic distillation can comprise the effluent from the hydrolysis of ethylene glycol carboxylate esters, suitably after removal of water and carboxylic acid, which effluent will contain not only the ethylene glycol monoester and generally the ethylene glycol diester but will also contain varying amounts of ethylene glycol. Thus, the reaction mixture from which the ethylene glycol is to be separated can be prepared by partially hydrolyzing mono-or di-carboxylate esters of ethylene glycol, or mixtures of said esters, by heating the ester or esters in the presence of water. Although the hydrolysis reaction will take place solely under the influence of heat, it may be preferred, in order to increase the rate of reaction, to effect hydrolysis in the presence of an acidic hydrolysis catalyst.

The feed to the hydrolysis operation can consist essentially of the monoester, or of the diester, or of mixtures of mono- or diesters in any proportion. The effluent from reactions which produce ethylene glycol monoester or ethylene glycol diester, or mixtures of the two, can be fed to the hydrolysis reaction. Typical reaction effluents of this nature are described, for example, in the above-mentioned Belgian Pat. No. 738,104, wherein the monoester is produced in the presence of substantial quantities of the diester, and in British Pat. No. 1,124,862, wherein the production of monoester substantially free from diester is disclosed. The hydrolysis step can be applied to glycol esters produced in any manner, whether by the process of the Belgian patent or the British patent or by various other processes. The hydrolysis reactions, regardless of the exact composition of the feed, continue until an equilibrium mixture comprising diester, monoester, ethylene glycol, carboxylic acid and water is formed. Before feeding the hydrolysis reaction product to the azeotropic distillation, the water and carboxylic acid are preferably removed from the hydrolysis effluent, e.g., by distillation in any convenient manner, these two compounds being readily separated from the ethylene glycol and the lower carboxylate esters. In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it may be preferred, in order to increase the rate of reaction, to effect hydrolysis in the presence of small amounts of an acidic hydrolysis catalyst such as a mineral acid, e.g., sulphuric acid and phosphoric acid, but most preferably a solid catalyst, e.g., in the form of an acidic ion exchange resin, is employed, as described in the previously-mentioned Golden U.S. Pat. No. 3,809,724. The hydrolysis step is thus suitably carried out by causing the glycol ester or ester mixture to react under the influence of heat (with or without a catalyst) to liberate (i.e., hydrolyze) from 15 to 80 mol % of the acyl moieties, e.g., acetate moieties, as lower carboxylate acid, e.g., acetic acid, desirably using at least 0.25 mol of water, preferably 0.75 to 5 mols of water, per equivalent of acyl moiety present in the hydrolysis feed. In the course of the hydrolysis, ethylene glycol is liberated.

Hydrolysis reaction temperatures of at least about 50° C are generally used but, when catalysts are employed, temperatures as low as 25° C can be satisfactorily used. It is generally not desirable to employ hydrolysis reaction temperatures above about 250° C. Preferably, temperatures of about 50° C to about 200° C are employed. Pressure is not critical as long as it is sufficient at the prevailing temperature to keep the reaction mixture in the liquid phase. Thus, pressures of as little as 50 mm.Hg can be employed as also can pressures of several thousand psia. Residence time of reactants and products within the hydrolysis zone is not critical. Thus, for example, residence times from as little as 1 minute up to and including several hours, e.g., 4 hours, or longer are entirely feasible.

Following the hydrolysis reaction, the hydrolyzate, which contains carboxylic acid, e.g., acetic acid, and water, in addition to ethylene glycol, monoesters, and diesters, is, as mentioned, suitably passed into a distillation column wherein a major portion of the carboxylic acid and water is vaporized and removed as overhead for subsequent recovery. This separation can be carried out in any conventional distillation column, such as used for the azeotropic distillation. In general, it is desirable to separate at least 90% of the water and carboxylic acid present in the mixture before proceeding with the removal and recovery of the ethylene glycol by azeotropic distillation. Although the distillation step to separate water and carboxylic acid can be carried out over a wide range of conditions, it has been found preferable to operate at pot or reboiler temperatures of 170° to 240° C and at pressures of from 400 mm.Hg to 50 psig. It will be understood that the water and carboxylic acid can be removed in a single distillation operation or the distillation may be carried out in two distillation zones in series with the water and some of the carboxylic acid being removed in the first distillation zone and the remainder of the carboxylic acid to be removed being separated in the second distillation zone. This distillation step is suitably carried out in conventional manner and the selection of specific conditions for treatment of specific feeds to separate specific amounts of water and carboxylic acid will be readily apparent to persons skilled in the art.

The above-described hydrolysis and preliminary distillation are suitably carried out in the manner discussed and exemplified in Golden U.S. Pat. No. 3,809,724.

Figure 2:
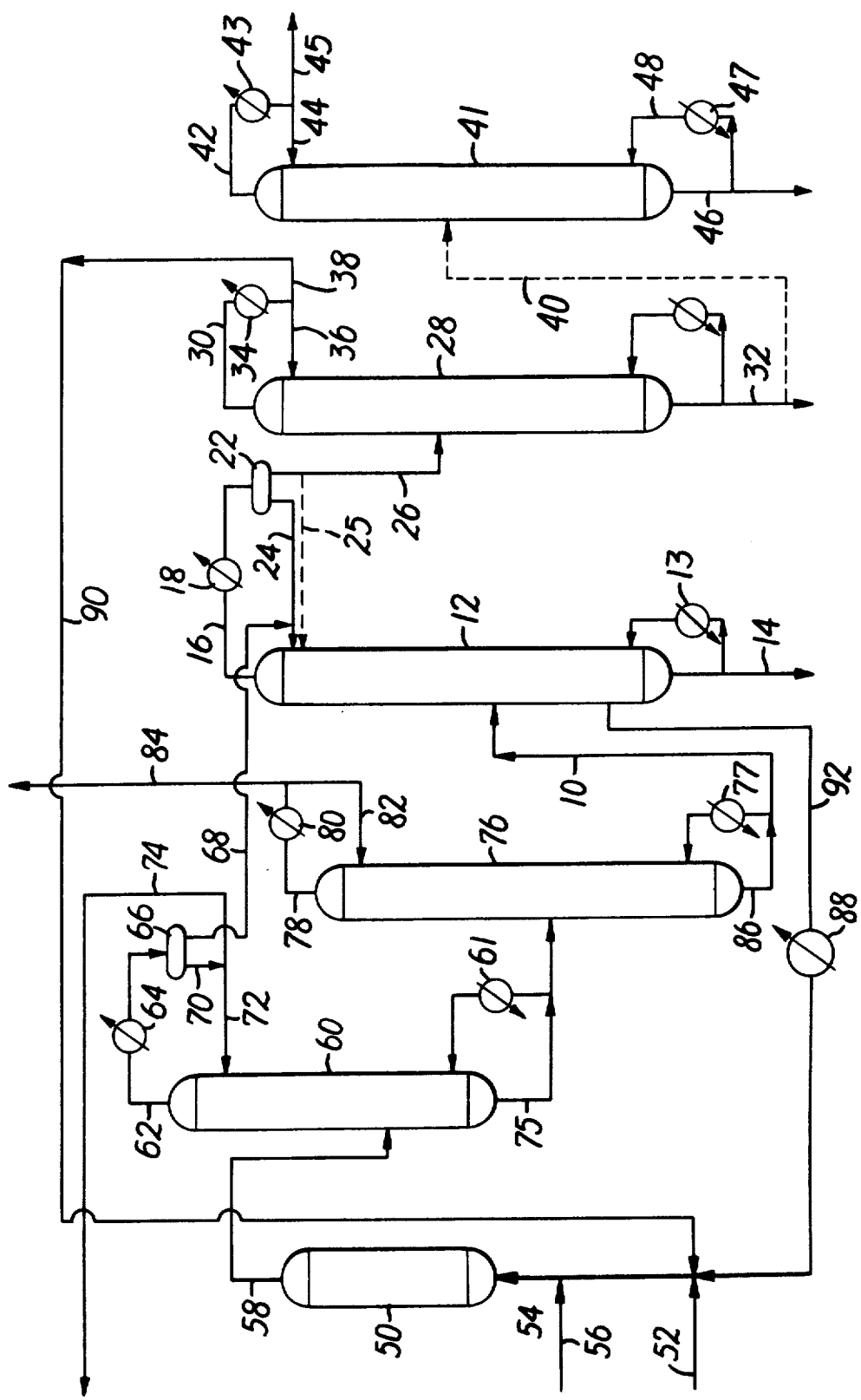

The invention will be more fully understood by reference to the accompanying drawing, wherein:

FIG. 1 is a diagrammatic view of an ethylene glycol recovery system embodying the azeotropic distillation system of the invention, and FIG. 2 is a similar diagrammatic view of an overall system wherein the azeotropic distillation recovery system is integrated with an ethylene glycol ester hydrolysis.

Referring to the drawing, and more particularly to FIG. 1, an ester feed stream comprising an ethylene glycol ester mixture is fed through line 10 to azeotropic distillation zone 12 which, in the embodiment illustrated, is a distillation column suitably provided with heating means, e.g., a convenient reboiler 13 and with a bottoms withdrawal line 14 and an overhead vapor line 16, the latter being connected to a condenser 18. The ethylene glycol is removed through line 16 in the form of an azeotrope with the azeotroping agent, and glycol ester is withdrawn through line 14. The overhead vapor from column 12 leaves through line 16 and is condensed in condenser 18, flows to a phase-separator 22, and the condensed azeotroping agent is returned to column 12 through line 24 as reflux, whereas the ethylene glycol phase is withdrawn through line 26 and is introduced into a refining column 28, also provided with a heating means, suitably in the form of a reboiler 29. A portion of the ethylene glycol phase may be returned to zone 12 as reflux if desired, as disclosed in the above-mentioned application of Chun Fei Chueh (Case 1088), the disclosure of which is incorporated herein by reference. In column 28, ethylene glycol ester and azeotroping agent contained in the ethylene glycol phase withdrawn from phase separator 22 is removed as vapor through line 30, and ethylene glycol in substantially purified form is withdrawn as bottoms through line 32. The vapors in line 30 are condensed in condenser 34 and a portion is returned as reflux to column 28 through line 36 and the remainder is withdrawn through line 38. Portions of the material in line 38 may, if desired, be combined with the feed to column 12, and make-up azeotroping agent, as required, may be added through line 10 or added to line 24. Preferably, the purified ethylene glycol withdrawn through line 32 is given a final distillation to insure against the presence in the product of higher boiling materials such as diethylene glycol and the like, which may tend to form in small amounts. Thus, if this further distillation is desired, the ethylene glycol from line 32 is passed through line 40 into distillation column 41 which is operated at pot or reboiler temperatures of 120° to 190° C and pressures of 50 mm to 60 mm to remove purified glycol through line 42 leading to condenser 43, the condensate from which is partially returned to column 41 as reflux through line 44, and the remainder is withdrawn as product glycol through line 45. The heavier components separated by the distillation are removed through line 46. The reboiler 47 in line 48 provides the necessary heat for maintenance of the distillation.

Referring now to FIG. 2, wherein the azeotropic distillation system just described is integrated with the hydrolysis of lower carboxylate esters of ethylene glycol to provide the feed to axeotropic distillation column 12, a hydrolysis ester feed stream enters a hydrolysis zone 50 through line 52 and line 54 and water for the hydrolysis enters through line 56 and is combined with the hydrolysis ester feed in line 54 before entering zone 50. Zone 50 is suitably filled with a bed of solid hydrolysis catalyst, e.g., a bed of acidic ion exchange resin and the combined water and ester feed stream flows upwardly through the bed and the hydrolyze reaction product is removed through line 58. The product stream in line 58 is introduced into a water separation column 60, provided with a reboiler 61 or other heating means. In column 60, water is vaporized and, along with a small amount of carboxylic acid, is withdrawn through line 62 and condensed in condenser 64. Since, in the embodiment illustrated in FIG. 2, the condensate from condenser 64 will contain some azeotroping agent, as will be explained below, the condensate passes to a phase separator 66 wherein the water and carboxylic acid form one phase and the azeotroping agent forms a second phase, the latter being withdrawn from separator 66 through line 68. The aqueous phase is withdrawn through line 70, with part of it being returned to column 60 through line 72 as reflux and the remainder being recycled to reactor 50 through line 74 which empties into water supply 56. The portion of the hydrolysis product stream supplied to column 60 which is not vaporized and withdrawn through line 62 and which comprises ethylene glycol, carboxylic acid and lower carboxylate esters of ethylene glycol is withdrawn through line 75 and fed to a distillation column 76, also provided with appropriate heating means, e.g., a reboiler 77. In distillation column 76, the carboxylic acid is vaporized and carboxylic acid vapors are withdrawn through line 78 and condensed in condenser 80 with some of the condensate being returned to column 76 as reflux through line 82 and the remainder being withdrawn from the system through line 84. The carboxylic acid stream will also contain any water which was not separated in column 60. The essentially water- and carboxylic acid-free ethylene glycol-lower carboxylate ester mixture is withdrawn from distillation zone 76 through line 86 and is supplied to line 10 to provide the ester feed to azeotropic distillation zone 12, as described above in connection with the discussion of FIG. 1. To complete the integration of the azeotropic distillation system with the hydrolysis system, a line 90 connects with line 38 to conduct the withdrawn condensate containing azeotroping agent from column 28 to the feed to hydrolysis zone 50 and a side stream from column 12 comprising vapors of lower carboxylate esters of ethylene glycol is withdrawn through line 92 and also combined with the feed of the hydrolysis zone, after being condensed by condenser 88.

The following examples of specific application will serve to give a fuller understanding of the invention but it will be understood that these examples are illustrative only and are not intended as limiting the invention.

EXAMPLE 1

Using a distillation column of 30 theoretical plates 2 inches diameter, there was fed continuously to the 12th plate of the column at the rate of 2200g/hr. an impure ethylene glycol composed of 34.6 mol % of ethylene glycol (EG), 4.2 mol % of ethylene glycol monoacetate (EGMA), 12.8 mol % of ethylene glycol diacetate (EGDA), 7.9 mol % ethylene glycol monoformate (EGMF) and 2.5 mol % ethylene glycol acetate formate (EGAF). This column was operated under a pressure of 30 psig with a bottoms or reboiler temperature of 228° C and an overhead temperature of 213° C. The feed mixture was azeotropically distilled in the column under the conditions indicated in the presence of tertiary butyltoluene as an azeotropic distillation solvent. The distillation was operated with total reflux of the azeotropic solvent and with reflux of the ethylene glycol phase at a reflux ratio of 3:1. During steady-state operation the azeotropic solvent introduced on the top plate gave a mol ratio of solvent to total vapor at the top of the column of about 55% and this gave 0.1 to 1 mol % of solvent in the reboiler. The product ethylene glycol recovered from the distillate was free of diester and showed an ethylene glycol to monoacetate ratio of 12:1 and a corresponding reduction in monoformate. More than 95% of the ethylene glycol fed to the distillation was recovered in the distillate.

EXAMPLE 2

Using the column and feed described in Example 1, the column was operated under a pressure of 5 psig with a bottoms or reboiler temperature of 208° C and an overhead temperature of 190° C. The feed mixture was azeotropically distilled in the column under the conditions indicated in the presence of isodurene as an azeotropic distillation solvent. The distillation was operated with total reflux of the azeotropic solvent and with reflux of the ethylene glycol phase at a reflux ratio of 2.1:1. The product ethylene glycol recovered from the distillate was free of diester and showed an ethylene glycol to monoacetate ratio of 12:1 and a corresponding reduction in monoformate, and 96% of the ethylene glycol fed to the distillation was recovered in the distillate.

Substantially pure ethylene glycol is readily obtained by fractional distillation of the ethylene glycol-containing product phase produced in the above-described azeotropic distillations. To effect this fractional distillation, the ethylene glycol-containing phase is continuously introduced into a fractional distillation column of the type used for the azeotropic distillation with 18 theoretical plates above the feed point and 22 theoretical plates below the feed point. This column is operated at a reduced pressure of about 150 mm.Hg with a bottoms or reboiler temperature of about 170° C and an overhead temperature of about 125° C, employing a reflux ratio of 2.3:1. More than 96% of the ethylene glycol in the feed to this distillation is recovered as the bottoms product and is in substantially purified form.

In order to increase the purity of the ethylene glycol even further, the overhead from the just-described distillation is continuously supplied to a fractional distillation column of the same type having 25 theoretical plates below the feed point and 15 theoretical plates above the feed point. This column is operated at a reduced pressure of about 150 mm.Hg with an overhead temperature of 170° C, using a reflux ratio of 2.1:1. More than 98% of the feed is withdrawn as purified ethylene glycol, 1% is withdrawn as bottoms and 1% as a light overhead fraction.

By reason of the use of the azeotropic distillation agents in accordance with the invention, the ethylene glycol recovered has favorable ultra violet characteristics, i.e., it exhibits low ultra violet absorbance. If desired, even greater purity can be ensured by adding small amounts of aqueous acetic acid and/or formic acid in the distillation following the azeotropic distillation, as disclosed in the application of Mitchell Becker and Charles C. Yang, being filed on even date herewith, and identified as Case 1091, the disclosure of which application is incorporated herein by reference. As disclosed in that application, the aqueous acid is suitably introduced into the distillation column below the point of introduction of the feed, suitably in amounts of 0.5 to 10% of water, 0.02 to 2.5% of formic acid and/or 0.02 to 5% of acetic acid, based on the weight of the feed.

As previously mentioned, while the invention has been primarily described and illustrated with reference to the recovery of ethylene glycol, similar results are obtained when the ethylene glycol is replaced by propylene glycol. Thus, in the case of the azeotropic distillation, use is made of azeotroping agents of the character indicated which form minimum-boiling azeotropes with propylene glycol, which azeotropes generally have a slightly lower boiling point than the corresponding azeotropes of the azeotroping agents with ethylene glycol. For example, with propylene glycol p-tertiary butyl toluene forms an azeotrope boiling at 169° C.

It will be understood, therefore, that all matter contained in the foregoing description and illustrated in the drawing is to be interpreted as illustrative only and not as limitative of the invention and various changes and modifications which will be apparent to those skilled in the art may be made without departing from the scope of the invention as defined in the appended claims.

I claim:

1. A process for recovering ethylene glycol or propylene glycol characterized by low ultraviolet absorbance from a complex mixture comprising propylene glycol or ethylene glycol in admixture with at least one mono-lower carboxylate ester and at least one di-lower carboxylate ester of said propylene glycol or ethylene glycol, said glycol and said esters tending to form azeotropic mixtures among themselves, which comprises the steps of:
    a. subjecting said complex mixture to distillation in a distillation zone in the presence of an azeotroping agent effective to form a minimum-boiling azeotrope with said glycol, said azeotroping agent being a hydrocarbon which is essentially water-immiscible and has a boiling point at atmospheric pressure of above 190° to about 220° C and is characterized by being free from hydrogen atoms attached to secondary or tertiary carbon atoms contained in an open chain, whereby an overhead product and a bottoms product are produced, said overhead product comprising an azeotrope of said azeotroping agent and said glycol and said bottoms product comprising at least some of the esters in said mixture substantially reduced in glycol content;
    b. separating said overhead product into a first phase comprising said azeotroping agent and a second phase comprising said glycol;
    c. returning said first phase to said distillation zone as reflux; and
    d. recovering purified glycol characterized by low ultraviolet absorbance from at least part of said second phase.

2. A process for recovering ethylene glycol or propylene glycol characterized by low ultraviolet absorbance from a complex mixture comprising propylene glycol or ethylene glycol in admixture with at least one mono-lower carboxylate ester and at least one di-lower carboxylate ester of said propylene glycol or ethylene glycol, said glycol and said esters tending to form azeotropic mixtures among themselves, which comprises the steps of:
    a. subjecting said complex mixture to distillation in a distillation zone in the presence of an azeotroping agent effective to form a minimum-boiling azeotrope with said glycol, said azeotroping agent being a hydrocarbon which is essentially water-immiscible and has a boiling point at atmospheric pressure of about 190° to about 220° C and is characterized by being free from hydrogen atoms attached to secondary or tertiary carbon atoms contained in an open chain, whereby an overhead product and a bottoms product are produced, said overhead product comprising an azeotrope of said azeotroping agent and said glycol and including some of said mono-lower carboxylate ester, and said bottoms product comprising said di-lower carboxylate ester substantially reduced in glycol content;
    b. separating said overhead product into a first phase comprising said azeotroping agent and a second phase comprising said glycol;
    c. returning said first phase to said distillation zone as reflux; and
    d. recovering purified glycol characterized by low ultraviolet absorbance from at least part of said second phase.

3. A process as defined in claim 2, wherein said second phase is fractionally distilled to remove said mono-lower carboxylate ester and any azeotroping agent present as an overhead distillate and to provide a bottoms product containing substantially only ethylene glycol or propylene glycol.

4. A process as defined in claim 1, wherein said second phase is fractionally distilled to remove said mono-lower carboxylate ester and any azeotroping agent present as an overhead distillate and to provide a bottoms product containing substantially only ethylene glycol or propylene glycol.

* * * * *